(12) United States Patent
Lussigny et al.

(10) Patent No.: US 11,767,307 B2
(45) Date of Patent: Sep. 26, 2023

(54) LITTER FOR PROMOTING PET'S IN-LITTER ELIMINATION

(71) Applicant: SPECIALITES PET FOOD, Elven (FR)

(72) Inventors: Marc-Henry Lussigny, Rennes (FR); Cécile Petel, Hennebont (FR)

(73) Assignee: SYMRISE AG, Holzminden (DE)

( * ) Notice: Subject to any disclaimer, the term of this patent is extended or adjusted under 35 U.S.C. 154(b) by 512 days.

(21) Appl. No.: 16/963,423

(22) PCT Filed: Jan. 29, 2019

(86) PCT No.: PCT/EP2019/052099
§ 371 (c)(1),
(2) Date: Jul. 20, 2020

(87) PCT Pub. No.: WO2019/145557
PCT Pub. Date: Aug. 1, 2019

(65) Prior Publication Data
US 2021/0087161 A1    Mar. 25, 2021

(30) Foreign Application Priority Data
Jan. 29, 2018 (EP) .................... 18305079

(51) Int. Cl.
| | | |
|---|---|---|
| *A01K 1/015* | (2006.01) | |
| *C07D 317/18* | (2006.01) | |
| *C07F 9/06* | (2006.01) | |
| *B01J 20/12* | (2006.01) | |
| *B01J 20/22* | (2006.01) | |
| *B01J 20/10* | (2006.01) | |
| *B01J 20/28* | (2006.01) | |
| *B01J 20/32* | (2006.01) | |

(52) U.S. Cl.
CPC .......... *C07D 317/18* (2013.01); *A01K 1/0154* (2013.01); *A01K 1/0155* (2013.01); *B01J 20/12* (2013.01); *B01J 20/22* (2013.01); *C07F 9/062* (2013.01); *B01J 20/103* (2013.01); *B01J 20/28023* (2013.01); *B01J 20/32* (2013.01)

(58) Field of Classification Search
None
See application file for complete search history.

(56) References Cited

U.S. PATENT DOCUMENTS

| | | | |
|---|---|---|---|
| 4,263,873 A | 4/1981 | Christianson | |
| 4,859,709 A * | 8/1989 | Rawlins | A61K 9/4866 514/420 |
| 5,415,131 A | 5/1995 | Dodman | |
| 2017/0369465 A1 * | 12/2017 | Guerret | A61K 31/19 |

FOREIGN PATENT DOCUMENTS

| | | |
|---|---|---|
| EP | 0 163 178 A2 | 12/1985 |
| WO | WO 91/10357 A1 | 7/1991 |
| WO | WO 2016/170475 A1 | 10/2016 |

OTHER PUBLICATIONS

International Search Report for International Application No. PCT/EP2019/052099, dated Apr. 24, 2019.

* cited by examiner

*Primary Examiner* — Brian Gulledge
(74) *Attorney, Agent, or Firm* — Birch, Stewart, Kolasch & Birch, LLP

(57) ABSTRACT

The present invention concerns a pet litter comprising a composition comprising 2,2-dimethyl-1,3-dioxolane-4-methanol. The present invention further relates to methods and uses of a composition comprising 2,2-dimethyl-1,3-dioxolane-4-methanol in pet litters, in particular for promoting in-litter elimination by pets.

15 Claims, No Drawings

LITTER FOR PROMOTING PET'S IN-LITTER ELIMINATION

The present invention generally relates to the field of pet litters.

More precisely, the present invention concerns the use of a specific composition in pet litter as an in-litter pet elimination promoter.

BACKGROUND OF THE INVENTION

Litters have been developed for elimination of urine and fecal matter, in particular for household pets. These litters contain an absorbent material, which aims to collect, bind and possibly decompose the matter to be absorbed. Pet litter is typically poured into a box and can then be removed from the container after use. Pet litter has to be replaced regularly by the pet owner.

Out-litter elimination or house soiling is the most common behaviour problem of pets reported by their owners. House-soiling can be explained by environmental and social factors, marking behaviours, medical problems etc. Often, the household pet will outright reject the litter formulation; and such rejection is indicated by undesired droppings and waste messes anywhere in the household. A serious and regularly encountered problem thus relates to the undesirable elimination out of the litter.

Several products in the market claim to attract pets to the litter for elimination purposes. Most of the time, either these products have not been tested in an unbiased and scientific manner or these products might attract pets generally but not in the context of urine or fecal elimination.

Patent application No. WO2016/170475 relates to the use of L-Felinine to attract a cat to eliminate in a litter. According to the disclosure thereof, 21 commercial cat attractants, including L-Felinine, were tested so as to evaluate the preference of the cats to eliminate urine and feces in a litter versus a control. Only L-Felinine was significantly preferred by cats for urine elimination.

There is therefore a serious need for new products which could efficiently serve as in-litter pet elimination promoters by drawing the animal to using and eliminating into the litter.

Definitions

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 (from 0.1 to 1) represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Moreover, the terms "at least", "less than" or "more than" encompass the hereafter cited value. For example, "at least 5%" has to be understood as also encompassing "5%".

Moreover, in the present invention, measurable values, such as an amount, have to be understood as encompassing standard deviations which can easily be determined by the skilled person in the technical domain of reference. Preferably, these values are meant to encompass variations of ±2%, more preferably ±1% from the specified value, as such variations are appropriate to reproduce the disclosed methods and products.

The term "about" as used herein when referring to a measurable value, such as an amount, is meant to encompass variations of ±5%, more preferably ±2%, even more preferably ±1% from the specified value, as such variations are appropriate to reproduce the disclosed methods and products. Accordingly, the term about can encompass variations larger than the standard deviations discussed above. Of course, when using "about", it is meant that embodiments obtained when strictly respecting the indicated values are also encompassed.

In the present disclosure, all of the possible ranges have not been explicitly mentioned so as to avoid having to set out at length and describe each and every value within the range. However, the ranges and ratio limits recited herein are combinable. For example, if ranges of 1-20 and 5-15 are recited for a technical feature, it is understood that ranges of 1-5, 1-15, 5-20 or 15-20 are also contemplated and encompassed thereby. This also applies on values illustrating lower and upper limits. A value illustrating a lower limit is thus combinable with a value illustrating an upper limit so as to form a ratio. For example, if a particular embodiment relates to the ratio X being superior to 2 and another particular embodiment relates to the ratio X being inferior to 5, it is understood that range of 2-5 is also contemplated and encompassed thereby.

Similarly, the words "comprise", "comprises", and "comprising" are to be interpreted inclusively. Likewise, the terms "include", "including" and "or" should all be construed to be inclusive. All these terms however have to be considered as encompassing exclusive embodiments that may also be referred to using words such as "consist of".

The methods and products and other embodiments exemplified here are not limited to the particular methodologies, protocols, and reagents that are described herein because, as the skilled artisan will appreciate, they may vary.

Unless defined otherwise, all technical and scientific terms, terms of art, and acronyms used herein have the meanings commonly understood by the skilled artisan in the field(s) of the invention, or in the field(s) where the term is used. Although any products, methods, or other means or materials similar or equivalent to those described herein can be used in the practice of the present invention, the preferred products, methods, or other means or materials are described herein.

The present invention is dedicated to pets. In the context of the present invention, dogs and cats are preferred. The present invention is more precisely dedicated to cats.

The term "pet litter" refers to the material receiving the urine and fecal matter. The pet litter typically comprises at least an absorbent material, used to collect, bind and possibly decompose the matter to be absorbed. The pet litter has thus a sorption capacity sufficient to absorb animal waste. The sorption capacity is typically at least about 0.4 ml/g of pet litter, and more typically ranges from about 0.4 to about 2.4 ml/g of pet litter, even more typically, from about 0.8 to about 1.4 ml/g of pet litter. The pet litter is typically able to absorb at least 10 mL, more typically at least 20 mL, more typically at least 40 mL, more typically at least 100 mL of animal waste. Litters can encompass pads, i.e. sanitary coverings which are used to cover a part of the floor. However, a pet litter is usually contained in a box, i.e. any apparatus that can hold pet litter. The box is most of the time a container with a bottom wall and one or more side walls, and/or any apparatus configured for litter to be positioned thereon. As a non-limiting example, a box may be a rectangular box having side walls that have a height of at least about 15 cm.

The term "elimination" means urination and/or defecation by a pet.

The term "in-litter pet elimination promoter" means any material having the capacity of promoting, increasing the elimination, in particular urination, of pets into the litter. An "in-litter pet elimination promoter" is an "attractant", able to attract pet to the litter for elimination purposes.

The term "odor-inhibiting agent" means any material that inhibits, reduces and/or controls the formation of waste odor resulting from urine and fecal matters.

"Clumping" absorbent materials are materials which form clumps after contacting animal urine and then can be scooped out of the litter pan to reduce odor from urine. In comparison, "non-clumping" absorbent materials do not form clumps when in contact with urine.

DESCRIPTION OF SOME EMBODIMENTS OF THE INVENTION

The present inventors unexpectedly observed that a composition comprising 2,2-dimethyl-1,3-dioxolane-4-methanol was advantageously able to attract the pets to eliminate, in particular urinate, in the litter.

The present invention thus concerns a pet litter comprising a composition including 2,2-dimethyl-1,3-dioxolane-4-methanol.

This composition is advantageously an in-litter pet elimination promoter. The pet litter according to the invention is attractive to pets while at the same time pleasant to humans.

According to the present invention, the presence of 2,2-dimethyl-1,3-dioxolane-4-methanol in the composition is required. In a particular embodiment, 2,2-dimethyl-1,3-dioxolane-4-methanol is the only solvent of the composition. More particularly, the composition can consist of 2,2-dimethyl-1,3-dioxolane-4-methanol. In another particular embodiment, the composition further includes one or more other solvents than 2,2-dimethyl-1,3-dioxolane-4-methanol.

Preferably, the composition in the pet litter of the invention is a solution or is in a microencapsulated form. More preferably, the composition in the pet litter of the invention is a solution, i.e., a liquid composition.

In a particular embodiment, the composition comprises from about 30% to about 99.5% of solvent (or solvents for embodiments wherein more than the required 2,2-dimethyl-1,3-dioxolane-4-methanol solvent is present in the composition) by weight of the composition, preferably from 40% to 99.5% by weight of the composition, preferably from 50% to 99.5% by weight of the composition, preferably from about 70% to about 99% by weight of the composition, preferably from 70% to 99% by weight of the composition, preferably from about 70% to about 90% by weight of the composition, preferably from 70% to 90% by weight of the composition.

In particular, the litter comprises from about 0.01% to about 2% by weight, preferably from 0.01% to 1% by weight, more preferably from about 0.01% to about 0.5% by weight, more preferably from 0.05% to 0.5% by weight, of solvent or solvents for embodiments wherein more than the required 2,2-dimethyl-1,3-dioxolane-4-methanol solvent is present in the composition In a particular embodiment, the composition further comprises at least another ingredient selected from an odor-inhibiting agent, a fragrance, an anti-microbial agent, an agent for controlling pH, a dye, a coloring agent, a de-dusting agent, a disease detecting agent and/or another in-litter pet elimination promoter.

In a preferred embodiment, the composition further comprises an odor-inhibiting agent. More particularly, the composition can consist of 2,2-dimethyl-1,3-dioxolane-4-methanol and an odor-inhibiting agent. Preferably, the odor-inhibiting agent is an alkyl thiophosphoric triamide. Preferably, the alkyl thiophosphoric triamide is N-(n-butyl)-thiophosphoric triamide. Alkyl thiophosphoric triamide compounds, such as NBPT, are typical urease inhibitors. NBPT inhibits the hydrolysis of urea into carbon dioxide and ammonia. NBPT is known as being unstable and difficult to handle. However, it is advantageously soluble in 2,2-dimethyl-1,3-dioxolane-4-methanol. The composition comprising at least one alkyl thiophosphoric triamide and 2,2-dimethyl-1,3-dioxolane-4-methanol has the capacity of increasing the elimination of pets into the litter and has also stable odor inhibiting properties.

In particular, the at least one of alkyl thiophosphoric triamide can preferably be present in an amount from about 0.5% to about 70% by weight of the composition, preferably from 0.5% to 70% by weight of the composition, preferably from about 0.5% to about 50% by weight of the composition, preferably from 0.5% to 50% by weight of the composition, preferably from about 1% to about 30% by weight of the composition, preferably from 1% to 30% by weight of the composition.

In a preferred embodiment, the litter comprises from about 0.001% to about 0.3%, more preferably from 0.001% to 0.3%, more preferably from about 0.005% to about 0.3%, more preferably from 0.005% to 0.3%, more preferably from about 0.01% to about 0.3%, more preferably from 0.01% to 0.3%, more preferably from about 0.01% to about 0.1%, more preferably from 0.01% to 0.1%, by weight, of the at least one alkyl thiophosphoric triamide.

In a particular embodiment, the composition further comprises a fragrance, preferably a fragrance that does not impact the advantageous previously cited functional properties of the composition.

Typically, the pet litter further comprises an absorbent material (also referred to herein, with respect to any embodiment of the present invention, as a "pet litter absorbent material"). The absorbent material can be any absorbent material commonly used in litters. Typically, the absorbent material is granular. Preferably, said absorbent material is selected from the group consisting of clays, silica gels, woods (such as pine, aspen, cedar, fir, spruce), agricultural products, and combinations thereof. Preferably, said absorbent material is selected from the group consisting of clays, silica gels, and combinations thereof. In a particular embodiment, the absorbent material is clay, such as calcium or sodium montmorillonite (including sodium bentonite), smectite, ventriculite, attapulgite, opal clay and/or kaolin. The absorbent material, in particular clays, can be clumping and/or non-clumping. It has been advantageously demonstrated that when the composition in the pet litter of the invention comprises an odor-inhibiting agent, the production of ammonia (inducing waste odors) is considerably reduced regardless of the absorbent material and regardless of the clumping and non-clumping properties thereof.

The composition in the pet litter of the invention can thus be combined with the absorbent material. In particular, the composition is homogeneously combined with the absorbent material.

In a preferred embodiment, the composition in the pet litter according to the invention is coated on at least a part of the absorbent material. For example, the composition can be sprayed onto at least a part of the absorbent material. Indeed, it has been observed that the effect is similar whatever the proportion of absorbent material coated with the composition. Preferably, the composition in the pet litter according to the invention is coated on at least 10% of the absorbent material, or on at least 20% of the absorbent material, or on at least 30% of the absorbent material, or on at least 40% of the absorbent material, or on at least 50% of the absorbent material, or on at least 60% of the absorbent material, or on at least 70% of the absorbent material.

In another particular embodiment, the litter comprises another material mixed with the absorbent material, the composition being coated onto said other material. For example, the composition can be sprayed onto the other material.

The pet litter can comprise an additive selected from the group consisting of a fragrance, an anti-microbial agent, an anti-sticking agent, an agent for controlling pH, a dye, a coloring agent, a de-dusting agent, a disinfectant, a disease detecting agent and/or another in-litter pet elimination promoter.

In a particular embodiment, the pet litter comprises from 0.005% to 10% of the composition as described above. Preferably, the pet litter comprises from 0.005% to 5%, more preferably from 0.05% to 5%, more preferably from 0.05% to 3%, more preferably from 0.05% to 2%, more preferably from 0.05% to 1.5%, more preferably from 0.05% to 1% of the composition as described above.

Method of Preparing Pet Litter

Another aspect of the present invention concerns a method of preparing a pet litter, the method comprising combining an absorbent material (typically used in pet litters) with a composition as above described, which comprises 2,2-dimethyl-1,3-dioxolane-4-methanol.

In a preferred embodiment, the absorbent material is combined with the composition by applying the composition onto at least a part of the absorbent material.

However, the composition can also be first applied onto at least a part of another material suitable for use in pet litter, and then the thus obtained material is further combined with the absorbent material by mixing.

The application of the composition onto the dedicated material (for example the absorbent material or another material) can be performed by using any appropriate method known by the skilled person. Preferably, the composition is applied by spraying it onto the material or by dripping drops of the composition onto the material (the composition is thus coated on the material).

Preferably, the application is performed at ambient temperature.

The composition as described above can be contained in a device configured to apply the composition on the dedicated material (for example the absorbent material or another material). In a first embodiment, the device is a spray recipient configured to spray the composition from a nozzle onto the material. In a second embodiment, the device is a solution dispenser for dripping drops of the composition onto the material (for example the absorbent material or another material), such as a dropper pipette.

The method of preparing a pet litter according to the invention can further comprise a step of adding an additive. The additive can be added at any stage, i.e. before, during, and/or after the combination of the absorbent material and the composition as described above.

Pet Litter Package

Another aspect of the present invention concerns a pet litter package comprising either a pet litter according to the present invention, or comprising a pet litter and a composition as above described for preparing a pet litter according to the invention.

Non-limiting examples of suitable containers include bags, litter boxes, cartons, bottles, packages of any type or design or material, and combinations thereof.

Uses

Another aspect of the present invention relates to the use of a composition as above described, as an in-litter pet elimination promoter, preferably as an in-litter pet urination promoter, in particular when combined with a pet litter.

The present invention also relates to the use of a pet litter according to the present invention, as an in-litter pet elimination promoter (or as an in-litter pet elimination-promoting means), preferably as an in-litter pet urination promoter (or, preferably, as an in-litter pet urination-promoting means).

An aspect of the invention also relates to a method of promoting in-litter elimination by a pet, the method comprising using in a pet litter a composition as above described to attract the pet to eliminate in said litter.

An aspect of the invention also relates to a method of promoting in-litter elimination by a pet, the method comprising exposing a pet litter comprising a composition comprising 2,2-dimethyl-1,3-dioxolane-4-methanol to the pet.

An aspect of the invention also relates to a method of promoting in-litter elimination by a pet, the method comprising using a pet litter of the invention to attract the pet to eliminate in said litter.

Alternatively, the invention can also be useful in a method of preventing out-litter elimination by a pet, the method comprising using in a pet litter a composition as above described to prevent the pet to eliminate out of said litter.

Yet alternatively, the invention can also be useful in a method of preventing out-litter elimination by a pet, the method comprising using a pet litter of the present invention to prevent the pet to eliminate out of said litter.

Indeed, as above mentioned, the inventors observed that, when used in a pet litter, the above-described composition is surprisingly and advantageously able to attract the pets to eliminate, in particular urinate, in the litter rather than out of the litter.

These methods can further comprise one or more steps selected from:

(i) preparing a pet litter as above described; and (ii) exposing the animal to the pet litter.

Attracting a pet to eliminate in a litter increases the frequency of urination, which in turn reduces the risk of urinary minerals aggregating into stones or crystallizing. Therefore, the composition as described above and/or the pet litter according to the invention can be used to treat, prevent or reduce the risk of urinary diseases in a pet, such as lower urinary tract disease ("FLUTD") and feline interstitial cystitis.

Another aspect of the present invention relates to the composition as described above and/or the pet litter according to the invention for use in the treatment of urinary disease in a pet, such as lower urinary tract disease ("FLUTD") and feline interstitial cystitis.

Another aspect of the present invention relates to the use in a pet litter of a composition comprising 2,2-dimethyl-1,3-dioxolane-4-methanol and at least one odor-inhibiting agent, preferably an alkyl thiophosphoric triamide, to inhibit pet waste odors emanating from said litter.

The invention also relates to a method for inhibiting pet waste odors, the method comprising using in a pet litter, a composition comprising 2,2-dimethyl-1,3-dioxolane-4- methanol and at least one odor-inhibiting agent, preferably an alkyl thiophosphoric triamide, wherein said composition inhibits pet waste odors emanating from said litter.

All above described particular embodiments of the composition contained in the pet litter according to the present invention, as well as of the pet litter itself, also apply to the methods and uses disclosed herein.

Kits

Another aspect of the present invention relates to a kit comprising, in one or more containers in a single package:
(i) an absorbent material (typically used in pet litters), and
(ii) a composition as above described.

Particular kits according to the present invention further comprise a means for communicating information or instructions, to help using the kits' elements.

EXAMPLES

Example 1: Materials

A composition A was prepared consisting of 2,2-dimethyl-1,3-dioxolane-4-methanol.

A composition B was prepared: about 25% of NBPT and about 75% of 2,2-dimethyl-1,3-dioxolane-4-methanol were combined and stirred at room temperature until being uniform.

A composition C was prepared: about 1% of NBPT and about 99% of 2,2-dimethyl-1,3-dioxolane-4-methanol were combined and stirred at room temperature until being uniform.

Example 2

Tests were performed in order to determine if the composition A consisting of 2,2-dimethyl-1,3-dioxolane-4-methanol influenced cat elimination behavior.

Twenty cats in 5 living rooms (4 cats per room) were involved in the study. The study lasted 4 days and two litter boxes containing two different products, i.e. a control cat litter (Litter 1, non-clumping clay) and an experimental cat litter (Litter 2) sprayed with 0.1% of composition A according to Example 1, were presented to the cats.

Diet was controlled for each test by measuring food intake. The temperature of the rooms was controlled. In each room, an equal proportion of males/females was respected.

The means of deposits weight on the first day are shown in Table 1.

TABLE 1

|  | $1^{st}$ day/Deposits weights |
|---|---|
| Litter 1 (control) | 218 |
| Litter 2 (experimental) | 321 |

On first day, the weight of Litter 2 was considerably higher than the weight of the control Litter 1, meaning that cats eliminated more in the experimental Litter 2 than in the control litter 1. This shows an in-litter cat elimination promoting (or attractant) effect of the composition A (consisting of 2,2-dimethyl-1,3-dioxolane-4-methanol) measured on non-soiled litters the first day of use.

Example 3

Tests were performed in order to determine if the composition B comprising NBPT and 2,2-dimethyl-1,3-dioxolane-4-methanol influenced cat elimination behavior.

Twenty cats in 5 living rooms (4 cats per room) were involved in the study. Two litter boxes containing two different products, i.e. a control cat litter (Litter 3, non-clumping clay) and an experimental cat litter (Litter 4) sprayed with 0.1% of composition B according to Example 1, were presented to the cats.

Diet was controlled for each test by measuring food intake. The temperature of the rooms was controlled. In each room, an equal proportion of males/females was respected.

The means of deposits weight on the first day are shown in Table 2.

TABLE 2

|  | $1^{st}$ day/Deposits weights |
|---|---|
| Litter 3 (control) | 162 |
| Litter 4 (experimental) | 263 |

On first day, the weight of Litter 4 was considerably higher than the weight of the control Litter 3, meaning that cats eliminated more in the experimental Litter 4 than in the control litter 3. This shows an in-litter cat elimination promoting (or attractant) effect of the composition measured on non-soiled litters the first day of use.

Example 4

Tests were performed in order to compare the performance of the composition C on various types of cat litters: a clumping clay litter, a non-clumping silica litter and a natural litter (vegetable fibers of fir and spruce).

Control cat litters were the commercial litters: a clumping clay litter (Litter 5), a natural litter (Litter 6), and a non-clumping silica litter (Litter 7). Experimental cat litters were prepared by spraying 3% of composition C of Example 1. A clumping clay litter (Litter 8), a natural litter (Litter 9), and a non-clumping silica litter (Litter 10) comprising composition C were thus obtained.

Synthetic urine and a urease from *Canavalia ensiformis* were added onto the control cat litters and onto the experimental cat litters.

The ammonia release of these control cat litters was determined by using an ammonia sensor (MultiRae) with a measurement error of ±1 ppm.

Results are shown in Table 3.

TABLE 3

|  | Amount of $NH_3$ (ppm) after 24 hours | Amount of $NH_3$ (ppm) after 54 hours |
|---|---|---|
| Litter 5 (control-clumping clay litter) | 165 | 240 |
| Litter 8 (experimental-clumping clay litter) | 1 | 2 |
| Litter 6 (control-natural litter) | 325 | 590 |
| Litter 9 (experimental-natural litter) | 1 | 2 |
| Litter 7 (control-non-clumping silica litter) | 46 | 101 |
| Litter 10 (experimental-non-clumping silica litter) | 1 | 2 |

Composition C is thus an efficient solution for reducing ammonia release by inhibiting urease activity, whatever the type of cat litter.

The invention claimed is:
1. A pet litter comprising a composition comprising 2,2-dimethyl-1,3-dioxolane-4-methanol.

2. The pet litter according to claim 1, wherein said composition further comprises an alkyl thiophosphoric triamide, preferably N-(n-butyl)-thiophosphoric triamide.

3. The pet litter according to claim 2, wherein the at least one alkyl thiophosphoric triamide is present in an amount from about 0.5% to about 50% by weight of the composition, wherein the term about encompasses variations of ±5%.

4. The pet litter according to claim 3, wherein the at least one alkyl thiophosphoric triamide is present in an amount from about 1% to about 30% by weight of the composition, wherein the term about encompasses variations of ±5%.

5. The pet litter according to claim 1, wherein the litter comprises from about 0.01% to about 2% by weight, of 2,2-dimethyl-1,3-dioxolane-4-methanol, wherein the term about encompasses variations of ±5%.

6. The pet litter according to claim 1, wherein the litter comprises from 0.01% to 1% by weight, of 2,2-dimethyl-1,3-dioxolane-4-methanol, wherein the term about encompasses variations of ±5%.

7. The pet litter according to claim 1, wherein the litter comprises from about 0.01% to about 0.5% by weight, of 2,2-dimethyl-1,3-dioxolane-4-methanol, wherein the term about encompasses variations of ±5%.

8. The pet litter according to claim 1, wherein the litter comprises from 0.05% to 0.5% by weight, of 2,2-dimethyl-1,3-dioxolane-4-methanol, wherein the term about encompasses variations of ±5%.

9. The pet litter according to claim 1, wherein said composition is a liquid composition.

10. The pet litter according to claim 1, further comprising an absorbent material.

11. The pet litter according to claim 10, wherein said absorbent material is selected from the group consisting of clays, silica gels, woods, agricultural products, and combinations thereof.

12. A method of promoting in-litter elimination by a pet, wherein said method comprises:

exposing a pet litter comprising a composition comprising 2,2-dimethyl-1,3-dioxolane-4-methanol to the pet.

13. The method of claim 12 wherein said elimination is urination.

14. A method of preparing a pet litter, wherein said method comprises combining an absorbent material with a composition comprising 2,2-dimethyl-1,3-dioxolane-4-methanol.

15. A kit comprising, in one or more containers in a single package:

(i) a pet litter absorbent material, and (ii) a composition comprising 2,2-dimethyl-1,3-dioxolane-4-methanol.

\* \* \* \* \*